United States Patent
Daniel et al.

(10) Patent No.: US 10,501,398 B2
(45) Date of Patent: Dec. 10, 2019

(54) CATALYTIC PERFORMANCE IN PROCESSES FOR PREPARING ACETIC ACID

(71) Applicant: BP Chemicals Limited, Middlesex (GB)

(72) Inventors: Berian John Daniel, East Yorkshire (GB); John Glenn Sunley, East Yorkshire (GB); Russell Alan Taylor, East Yorkshire (GB); Gareth Gerald Armitage, East Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 16/216,766

(22) Filed: Dec. 11, 2018

(65) Prior Publication Data

US 2019/0112253 A1 Apr. 18, 2019

Related U.S. Application Data

(62) Division of application No. 15/312,060, filed as application No. PCT/EP2015/063151 on Jun. 12, 2015, now Pat. No. 10,183,906.

(30) Foreign Application Priority Data

Jun. 20, 2014 (EP) .................................. 14173358

(51) Int. Cl.
| | | |
|---|---|---|
| C07C 51/347 | (2006.01) | |
| C07C 67/37 | (2006.01) | |
| C07C 67/54 | (2006.01) | |
| C07C 41/16 | (2006.01) | |
| C07C 51/09 | (2006.01) | |

(52) U.S. Cl.
CPC ............ *C07C 51/347* (2013.01); *C07C 41/16* (2013.01); *C07C 51/09* (2013.01); *C07C 67/37* (2013.01); *C07C 67/54* (2013.01)

(58) Field of Classification Search
CPC ......... C07C 67/37; C07C 41/16; C07C 51/09; C07C 51/347
See application file for complete search history.

(56) References Cited

U.S. PATENT DOCUMENTS

| | | | |
|---|---|---|---|
| 4,792,620 A * | 12/1988 | Paulik | B01J 31/0231 560/232 |
| 5,068,442 A * | 11/1991 | Ashina | C07C 209/16 564/474 |
| 6,521,783 B1 | 2/2003 | Wegman et al. | |
| 7,465,822 B2 | 12/2008 | Cheung et al. | |
| 2009/0107833 A1 | 4/2009 | Warner | |

FOREIGN PATENT DOCUMENTS

| | | |
|---|---|---|
| WO | WO 2008/132438 | 11/2008 |
| WO | WO 2008/132450 | 11/2008 |
| WO | WO 2008/132468 | 11/2008 |
| WO | WO 2009/045253 | 4/2009 |
| WO | WO 2011/027105 | 3/2011 |
| WO | WO 2011/027105 A1 * | 3/2011 |
| WO | WO 2013/124404 | 8/2013 |
| WO | WO 2013/124423 | 8/2013 |

OTHER PUBLICATIONS

Norskov et al, Nature Chemistry, Towards the Computational Design of Solid Catalysts, 2009, 1, pp. 37-46. (Year: 2009).*
Norskov et al., Nature Chemistry, "Towards the Computational Design of Solid Catalysts", 2009, 1, pp. 37-46.

* cited by examiner

*Primary Examiner* — Paul A Zucker
(74) *Attorney, Agent, or Firm* — McDonnell Boehnen Hulbert & Berghoff LLP

(57) ABSTRACT

In processes for the hydrolysis of a methyl acetate with at least one of water and methanol in the presence of at least one Brønsted acid catalyst to produce acetic acid the performance of the catalyst is improved by using a methyl acetate feed in which the total amount of acetaldehyde and 1,1 dimethoxyethane impurities is maintained at 100 ppm wt or less calculated as mass equivalents of acetaldehyde.

18 Claims, No Drawings

CATALYTIC PERFORMANCE IN PROCESSES FOR PREPARING ACETIC ACID

This application is a divisional application of U.S. application Ser. No. 15/312,060 filed on Nov. 17, 2016, now U.S. Pat. No. 10,183,906, which is a U.S. national phase application under 35 U.S.C. § 371 of International Patent Application no. PCT/EP2015/063151, filed on Jun. 12, 2015, which claims the benefit of Great Britain Application no. 14173358.4, filed on Jun. 20, 2014. The entirety of each of the foregoing applications is hereby incorporated by reference into the present specification.

The present invention relates to a process for improving the performance of solid acid catalysts in the production acetic acid from a methyl acetate containing feedstock using such catalysts. In particular, the invention relates to a process for improving the performance of Brønsted acid catalysts in the co-production of acetic acid and dimethyl ether from methyl acetate and methanol using such catalysts.

Methyl acetate may be hydrolysed to acetic acid in the presence of an acid catalyst and water. For example, it is also known from CN 1541991 that esters may be hydrolysed to the corresponding acid in the presence of an ammonium salt of a heteropolyacid, such as an ammonium salt of a phosphotungstic acid or a silicotungstic acid.

U.S. Pat. No. 6,521,783 describes a process in which acetic acid, methyl acetate, methanol, dimethyl ether and water are fed to a hydrolysis/dehydration reactor which contains an ester hydrolysis catalyst and an alcohol dehydration catalyst which can be the same or different. The alcohol dehydration catalyst can be selected from a solid acid, heteropolyacids, acidic zeolites, titania or silica promoted alumina, aluminium phosphate or tungsten oxide supported on silica-alumina. The ester hydrolysis catalyst can be selected from acidic ion-exchange resins, acidic gamma alumina, fluorinated alumina, sulphate or tungstate promoted zirconia, titania or silica promoted alumina, aluminium phosphate, tungsten oxide supported on silica-alumina, clays, supported mineral acids, zeolites or heteropolyacids.

WO 2011/027105 describes the use of acid zeolites to catalyse the dehydration and hydrolysis of mixtures of methanol and methyl acetate, such zeolites being said to possess a 10-membered ring channel and a 2 dimensional channel system.

WO 2013/124404 describes a process for the co-production of acetic acid and dimethyl ether from a mixture of methanol and methyl acetate by contacting the mixture at a temperature from 200 to 260° C. with a catalyst composition comprising a zelite possessing a 2-dimensional channel system comprising at least one channel having a 10-membered ring and a silica:alumina molar ratio of at least 22:1.

WO 2013/124423 describes a process for the co-production of acetic acid and dimethyl ether by contacting a mixture of methanol and methyl acetate with a zeolite catalyst possessing a 2-dimensional channel system comprising at least one channel having a 10-membered ring and having at least 5% of its cation exchange capacity occupied by one or more alkali metal cations.

As described above methyl acetate may be hydrolysed to acetic acid in the presence of acid zeolite catalysts and other solid Brønsted acid catalysts. Methyl acetate feedstock may be derived from processes for the carbonylation of ethers or may be supplied as a mixture with methanol as a byproduct from the hydrolysis of polyvinyl acetate to produce polyvinyl alcohol. In such processes, acetaldehyde and its precursor compounds, such as 1,1 dimethoxyethane, may be formed as unwanted by-products, generally as a result of side-reactions.

US 2009/0107833 describes a method of removing acetaldehyde from ternary mixtures of methyl acetate, methanol and acetaldehyde which includes a) feeding the mixture to a distillation column; b) distilling the mixture at a pressure of 10 psig or more to generate an overhead vapour stream enriched in acetaldehyde as compared with the feed mixture and a residue stream depleted in acetaldehyde as compared with the feed mixture; and c) withdrawing the residue stream deleted in acetaldehyde from the distillation column.

WO 2009/045253 describes a method for removing aldehyde impurities from a methyl acetate supply by reacting the supply with a polyol and converting the aldehyde impurities to cyclic acetals which can subsequently be removed by distillation.

It has now been found that the presence of acetaldehyde and its precursor compounds in solid acid catalysed processes for the production of acetic acid can have a deleterious effect on the catalytic performance (activity and/or lifetime) of the catalysts and, in particular on the performance of solid Brønsted acid catalysts, such as zeolites employed in such processes. The performance of these catalysts can be considerably improved by controlling the amount of acetaldehyde and its precursor compounds present in methyl acetate feedstocks to such processes. In particular, it has been found that by maintaining acetaldehyde and its precursor compounds in a total amount of up to about 100 ppm wt calculated as mass equivalents of acetaldehyde is particularly beneficial to catalyst lifetime.

Specific acetaldehyde precursor compounds found to be detrimental include the acetal, 1,1-dimethoxyethane. This acetal compound in the presence of solid Brønsted acid catalysts and methanol is a source of acetaldehyde and vice-versa via the equilibrium reaction:acetaldehyde+ 2methanol⇌1,1 dimethoxyethane+water.

Accordingly, the present invention provides a process for the hydrolysis of a methyl acetate feed with at least one of water and methanol in the presence of at least one Brønsted acid catalyst to produce acetic acid in which process the performance of the catalyst is improved by using as a feed to the process a methyl acetate feed in which the total amount of acetaldehyde and 1,1 dimethoxyethane impurities is maintained at 100 ppm wt or less calculated as mass equivalents of acetaldehyde.

Processes for the manufacture of methyl acetate include those in which dimethyl ether reactant is carbonylated with a carbon monoxide-containing gas to produce methyl acetate. Such processes are described in, for example U.S. Pat. No. 7,465,822, WO 2008/132438, WO 2008/132468 and WO 2008/132450. It has now been determined that acetaldehyde and/or its precursor compounds can be generated, via side-reactions, in such processes.

In some or all embodiments of the present invention, the methyl acetate feed for a process is derived from processes for carbonylating of dimethyl ether with a carbon monoxide-containing gas in the presence of a zeolite carbonylation catalyst.

In some or all embodiments of the present invention, the methyl acetate feed is derived from a process for carbonylating dimethyl ether with carbon monoxide-containing gas in the presence of a zeolite carbonylation catalyst wherein the carbon monoxide-containing gas is a synthesis gas.

Thus, the present invention further provides a process for the dehydration-hydrolysis of methyl acetate and methanol to co-produce acetic acid and dimethyl ether which process is integrated with a carbonylation process for the production of methyl acetate which integrated process comprises the steps:

a) carbonylating dimethyl ether with a carbon monoxide-containing gas in the presence of a zeolite carbonylation catalyst to produce a carbonylation reaction product and recovering methyl acetate therefrom;

b) pre-treating at least a portion of the methyl acetate recovered in step (a) to reduce the amount of acetaldehyde and 1,1 dimethoxyethane impurities therein;

c) converting methanol and methyl acetate by dehydration-hydrolysis in the presence of at least one Brønsted acid catalyst to co-produce acetic acid and dimethyl ether;

in which dehydration-hydrolysis process the performance of the catalyst is improved by using as a methyl acetate feed methyl acetate pre-treated in step (b) in which the total amount of acetaldehyde and 1,1 dimethoxyethane impurities is maintained at 100 ppm wt or less calculated as mass equivalents of acetaldehyde.

In some or all embodiments of the present invention, the total amount of acetaldehyde and 1,1 dimethoxyethane in a methyl acetate feed is maintained at 0 to 75 ppm wt or less, for example 0 to 50 ppm wt, preferably 0 to 25 ppm wt calculated as mass equivalents of acetaldehyde.

In some or all embodiments of the present invention the methyl acetate feed further comprises one of both of methanol and water. Suitably, the methyl acetate feed further comprises methanol and water.

In some or all embodiments of the present invention the methyl acetate feed further comprises one or more of carbon oxides, hydrogen and acetic acid.

Methyl acetate may be hydrolysed with at least one of water and methanol in the presence of a solid Brønsted acid catalyst to generate acetic acid The hydrolysis process may be carried out as a vapour phase process or as a liquid phase process, for example as a fixed bed process or a slurry phase process.

If it is desired to operate the hydrolysis process as a vapour phase process, it is preferable to volatilise liquid feed(s), for example in a pre-heater prior to contact with the Brønsted acid catalyst.

The hydrolysis process may be carried out at a temperature in the range 100° C. to 350° C. Preferably, hydrolysis processes conducted as liquid phase process are carried out at temperatures in the range 140° C. to 210° C. Preferably, vapour phase processes are conducted at temperatures in the range 150° C. to 350° C., for example in the range 200° C. to 280° C.

The hydrolysis process may be carried out at atmospheric pressure or at pressures greater than atmospheric.

Suitably, the hydrolysis process is carried out at a gas hourly space velocity (GHSV) in the range 500 to 40,000 $h^{-1}$.

Suitably, the hydrolysis process is carried out at a liquid hourly space velocity (LHSV) in the range 0.2 to 20 $h^{-1}$.

By 'Brønsted acid catalyst' is meant a solid acid catalyst which has the ability to donate an acidic proton to facilitate a chemical reaction.

In the present invention at least one solid Brønsted acid is utilised to catalyse one or both of the hydrolysis and dehydration processes.

In some or all embodiments of the present invention at least one solid Brønsted acid catalyst is a zeolite.

In some or all embodiments of the present invention at least one solid Brønsted acid catalyst is a heteropolyacid.

The term "heteropolyacid" as used herein and throughout the specification is meant to include the free acids. Heteropolyacids for use herein may be used either as free acids or as partial salts. Typically, the heteropolyacid, or the anionic component of its corresponding salt comprises 2 to 18 oxygen-linked polyvalent metal atoms, which are called peripheral atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for example cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters". The structures of some of the well-known anions are named after the original researchers in this field and are known, for example as Keggin, Wells-Dawson and Anderson-Evans-Perloff structures.

Heteropolyacids usually have a high molecular weight, for example in the range from 700-8500 and include dimeric complexes. They have a relatively high solubility in polar solvents such as water or other oxygenated solvents, especially if they are free acids and in the case of several salts, and their solubility can be controlled by choosing the appropriate counter-ions. Specific examples of heteropolyacids that may be utilised in the present invention include the free acids such as silicotungstic acids, phosphotungstic acids and 12-tungstophosphoric acid ($H_3[PW_{12}O_{40}].xH_2O$); 12-molybdophosphoric acid ($H_3[PMo_{12}O_{40}].xH_2O$); 12-tungstosilicic acid ($H_4[SiW_{12}O_{40}].xH_2O$); 12-molybdosilicic acid ($H_4[SiMo_{12}O_{40}].xH_2O0$ and ammonium salts of heteropolyacids, such as ammonium salts of a phosphotungstic acid or a silicotungstic acid Zeolites are useful as catalysts for the hydrolysis of methyl acetate to produce acetic acid and also for the dehydration of methanol to produce dimethyl ether. Certain zeolites are effective catalysts for both of these reactions. Thus, in the presence of these dual-effective zeolites, a feed comprising methyl acetate and one or both of methanol and water, the crude reaction product generated therefrom comprises the co-products acetic acid and dimethyl ether.

The hydrolysis of methyl acetate to produce acetic acid and dehydration of methanol to produce dimethyl ether can be represented by equations (1) and (2) respectively:

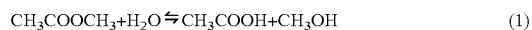

$$CH_3COOCH_3 + H_2O \leftrightarrows CH_3COOH + CH_3OH \quad (1)$$

$$2CH_3OH \leftrightarrows CH_3OCH_3 + H_2O \quad (2)$$

Zeolites useful as dehydration and hydrolysis catalysts include zeolites having framework structure types, FER (typified by ferrierite and ZSM-35) and MFI (typified by ZSM-5). The three-letter codes such as 'FER' refer to the framework stricture type of the zeolites using the nomenclature proposed by the International Zeolite Association. Information about structure codes and zeolites is available on the website of the International Zeolite Association at www.iza-online.org.

In some or all embodiments of the present invention, the solid Brønsted acid catalyst is at least one zeolite which comprises at least one channel having a 10-membered ring. In these embodiments, the zeolite comprising at least one channel having a 10-membered ring may have a framework type selected from FER and MFI. Thus, suitably a zeolite has the framework type FER and is selected from one or both of ferrierite and ZSM-35. Alternatively and/or additionally, a zeolite having framework type MFI such as ZSM-5 may be employed.

Zeolites for use in hydrolysis or dehydration-hydrolysis processes may be employed in an exchanged form. Exchanged forms of zeolites can be prepared by techniques such as ion-exchange and impregnation. These techniques are well-known in the art and typically involve the exchange of the hydrogen or ammonium cations of a zeolite with metal cations. For example, a zeolite may be in an exchanged form with one or more alkali metal cations, for example one or more of sodium, potassium or cesium. Suitably, an exchanged form zeolite is ferrierite exchanged with cesium or ZSM-35 exchanged with cesium.

The silica to alumina molar ratio of a zeolite is the bulk or overall ratio. This can be determined by any one of a number of chemical analysis techniques. Such techniques include x-ray fluorescence, atomic absorption and ICP (inductive coupled plasma). All will provide substantially the same silica to alumina molar ratio value.

The bulk silica to alumina molar ratio (herein also termed "SAR") of synthetic zeolites will vary. For example, the SAR of a zeolite, such as ferrierite, may range from as low as 5 to over 90. Suitably, the SAR of a zeolite utilised in the present invention may be of from 10:1 to 90:1, for example of from 20:1 to 60:1.

Suitably, a zeolite utilised in the present invention may be composited with a binder material. As will be appreciated by those of ordinary skilled in the art, binder materials are selected such that the zeolite catalyst is suitably active and robust under the reaction conditions employed. Examples of suitable binder materials include inorganic oxides, such as silicas, aluminas, alumina-silicates, magnesium silicates, magnesium aluminium silicates, titanias and zirconias. Preferred binder materials include aluminas, alumina-silicates and silicas, for example boehemite type alumina.

The relative proportions of the catalyst and binder material may vary widely but suitably, the binder material may be present in a composite in an amount in the range of 10% to 90% by weight of the composite, preferably, in the range of 10% to 65% by weight of the composite.

In general, zeolites are synthesised in the form of powders and as such may be formed into particles without the use of a binder. Typical zeolite catalyst particles include extrudates whose cross sections are circular or embrace a plurality of arcuate lobes extending outwardly from the central portion of the catalyst particles.

More than one Brønsted acid catalyst may be utilised in the present invention. Where it is desired to employ two or more different catalysts, such catalysts may be utilised in the form of alternating catalyst beds or as one or more intimately mixed catalyst beds.

The dehydration reaction generates water in-situ and this may be utilised in the hydrolysis reaction. However and preferably, additional water is supplied to the process. Suitably, water may be supplied in an amount of from 0.1 to 50 mol % based on the total feed of methyl acetate, methanol and water supplied to the process.

As noted above a suitable methyl acetate feed for the present invention may be derived from processes for the production of methyl acetate by carbonylating dimethyl ether with a carbon monoxide-containing gas in the presence of a zeolite carbonylation catalyst.

In addition to methyl acetate, components which can be present in a carbonylation reaction product include one or more of unreacted dimethyl ether, carbon monoxide, water, acetic acid, methanol and small amounts of acetaldehyde and/or 1,1 dimethoxyethane. If carbon dioxide and hydrogen are present in the carbonyltion process, for examples as components of the carbon monoxide-containing gas, the carbonylation reaction product may also comprise small quantities of carbon dioxide and hydrogen.

Methyl acetate may be recovered from such carbonylation reaction products by conventional gas-liquid separation techniques to form a stream of liquid methyl acetate which stream may besides methyl acetate contain one or more of dimethyl ether, water, acetic acid, methanol, carbon oxides, hydrogen and small amounts of acetaldehyde and/or 1,1 dimethoxyethane.

Typically, methyl acetate derived from such carbonylation processes may comprise 50 to 99 mol % methyl acetate, >0 to 45 mol % dimethyl ether and a total amount of acetaldehyde and 1,1 dimethoxyethane of more than 100 ppm wt or more than 500 ppm wt or more than 1000 ppm wt or more than 2000 ppm wt up to 1 wt %, calculated as mass equivalents of acetaldehyde. Small amounts of one or more of acetic acid, water, carbon oxides and hydrogen may also be present.

As would be recognized by the skilled person the amount of impurities such as acetaldehyde and 1,1 dimethoxyethane in a methyl acetate stream may be determined by conventional compositional analysis techniques such as gas chromatography and are generally detectable, depending on the specific gas chromatograph used, to levels of about 2 ppm or below.

The carbonylation process is carried out using any suitable carbon monoxide-containing gas. Suitably, the carbon monoxide-containing gas may be pure carbon monoxide or may be a mixture of carbon monoxide and hydrogen, suitably a synthesis gas. The carbon monoxide-containing gas or synthesis gas may further comprise carbon dioxide.

The partial pressure of carbon monoxide utilised in a carbonylation process should be sufficient to permit the production of methyl acetate. Suitable carbon monoxide partial pressures include those in the range 0.1 to 100 barg (10 kPa to 10,000 kPa).

If utilised in the carbonylation process, suitable hydrogen partial pressures include those in the range 1 barg to 100 barg (100 kPa to 10,000 kPa).

Dimethyl ether may employed at a concentration in the range of 1 mol % to 20 mol %, based on the total of all feed streams to the carbonylation process.

A suitable molar ratio of carbon monoxide to dimethyl ether is range 1:1 to 99:1.

Carbonylation of dimethyl ether may be carried out in the presence of a zeolite carbonylation catalyst. Suitable zeolite carbonylation catalysts include aluminosilicate zeolites which comprise at least one channel which is defined by an 8-member ring. The aperture of the zeolite channel system defined by the 8-membered ring should be of such dimensions that reactant dimethyl ether and carbon monoxide molecules can diffuse freely in and out of the zeolite framework. Suitably, the aperture of the 8-member ring channel of the zeolite has dimensions of at least 2.5×3.6 Angstroms. Non-limiting examples of suitable zeolites include those of framework type MOR (for example mordenite), FER (for example ferrierite), OFF (for example offretite) and GME (for example gmelinite).

In such carbonylation processes, the presence of significant amounts of water tends to inhibit the production of methyl acetate and thus it is preferred that the carbonylation is conducted under anhydrous conditions. This may be achieved by drying the dimethyl ether, carbon monoxide or other feeds prior to introduction into the process.

A carbonylation process may be carried out as vapour phase process. Suitably, the carbonylation process is carried out at a temperature of about 100° C. to 350° C. and at a total pressure of about 10 to 100 barg (1000 kPa to 10,000 kPa).

The level of acetaldehyde and 1,1 dimethoxyethane present in methyl acetate-containing streams intended to be used as feeds in processes of the present invention may be reduced to control or maintain the amount of these impurities to less than 100 ppm w/w by pre-treating the methyl acetate feed. Such pre-treatments include, for example one or more distillation methods, such as a fractional distillation method in a distillation column.

Thus, suitably a methyl acetate feed intended for use in the processes of the present invention is pre-treated, for example by a fractional distillation method to reduce the amount of impurities to less than 100 ppm wt or thereabouts calculated as mass equivalents of acetaldehyde. Preferably, a methyl acetate feed is pre-treated to reduce the amount of impurities to less than about 50 ppm wt.

Suitably, distillation of a mixture of methyl acetate, dimethyl ether and acetaldehyde/1,1 dimethoxyethane may be achieved by the steps of:
 (i) feeding the mixture to a distillation column;
 (ii) distilling the mixture to generate a heads stream depleted in acetaldehyde and precursor compounds as compared to the feed mixture, a base stream depleted in acetaldehyde and precursor compounds as compared to the feed mixture and a sidedraw stream enriched in acetaldehyde as compared to the feed mixture;
 (iii) withdrawing from the column the sidedraw stream enriched in acetaldehyde and precursor compounds at a point above the feed point of the feed mixture to the column.

Acetaldehyde and 1,1 dimethoxyethane are removed as volatile components as a sidedraw above the feed point of the feed mixture to the column, dimethyl ether is removed as a light component from the head of the column and methyl acetate is removed as a heavy component from the base of the column.

Suitably, the distillation column is operated at elevated pressure, such as at a pressure of from about 10 to 30 barg (1000 to 3000 kPa) and at a heads temperature of 45 to 90° C. or lower such as at a heads temperature of 40 to 90° C.

The feed mixture to the column may be fed as a vapour or as a liquid. Typically, the heads stream depleted in acetaldehyde and comprising mainly dimethyl ether is withdrawn as a vapour. The heads typically comprises at least 60 mol % dimethyl ether, for example 60 to 95 mol % or higher dimethyl ether. The heads vapour is typically condensed and a portion of the condensed liquid is returned to the column as reflux.

The column may be operated with a return of liquid reflux to the head of the column at a reflux to distillate ratio dependent upon such factors as the required overhead stream composition. At operating pressures of from 10 to 30 barg (1000 to 3000 kPa) and at an overhead vapour temperatures of 45 to 90° C. or 40 to 90° C., a suitable reflux ratio is in the range 1 to 4, for example 1.5 to 2.5. A suitable boil-up ratio may be in the range 2 to 8.

Suitably, the distillation column has at least 5, such as at least 15 theoretical stages, for example 20 to 60 theoretical stages. Since distillation columns may have differing efficiencies 15 theoretical stages may be equivalent to at least 25 actual stages with an efficiency of about 0.7 or at least 30 actual stages with an efficiency of about 0.5.

A sidedraw stream enriched in acetaldehyde/1,1 dimethoxyethane impurities is withdrawn from the column at a point above the feed point of the feed mixture to the column. Recovery of such impurities in the sidedraw stream can be enhanced by providing sufficient stripping capacity in the distillation column below the feed point of the feed mixture to the column. Thus, it is preferred that a distillation column has at least 3 theoretical stages, for example 3 to 10 theoretical stages, below the feed point of the feed mixture.

To optimise recovery of acetaldehyde in the sidedraw stream, it is preferred that the sidedraw stream is withdrawn from the column at the point of maximum concentration of acetaldehyde within the column. As would be recognised by the skilled person in the art, the point in the column at which the concentration of acetaldehyde will be at its highest is dependent upon the specific operating conditions employed and, in particular the specific pressure, temperature and reflux ratio employed. Concentrations of components within the column can be readily determined, for example by compositional analysis of the distillation mixtures at varying stages along the column, such as by gas chromatographic analysis techniques.

Typically, however, for a 40 stage column, the feed point of the feed mixture to the column may be at stages 10 to 25 counted from the head of the column and the sidedraw stream withdrawn at stages 4 to 15 counted from the head, provided that the sidedraw is withdrawn at a stage above the feed point stage to the column.

Preferably, the sidedraw stream is withdrawn from the column as a liquid. In addition to acetaldehyde, the sidedraw stream may further comprise amounts of one or both of dimethyl ether and methyl acetate The base stream depleted in acetaldehyde/1,1 dimethoxyethane as compared to the feed mixture comprises methyl acetate and generally comprises the majority of methyl acetate present in the feed mixture to the column.

Such distillation processes are effective to provide acetaldehyde contents in the base stream of 100 ppm wt or less, or 50 ppm wt or less where the feed mixture has a total acetaldehyde content of more than 100 ppm wt or more than or more than 200 ppm wt or more than 500 ppm wt or more than 1000 ppm wt or more than 2000 ppm wt up to 1 wt %, calculated as mass equivalents of acetaldehyde.

In one or more embodiments of the present invention, the total amount of acetaldehyde and 1,1 dimethoxyethane in the methyl acetate feed to dehydration-hydrolysis is maintained at 0 to 100 ppm wt, calculated as mass equivalents of acetaldehyde by pre-treating a methyl acetate recovered from carbonylation step (a) by a fractional distillation method.

For a feed mixture comprising >0 to 80 mol % methyl acetate, for example 50 to 80 mol %, a total amount of more than 100 ppm or more than 500 ppm wt or more than 1000 ppm or more than 2000 ppm up to 1 wt % of acetaldehyde and 1,1 dimethoxyethane and >0 to 50 mol % dimethyl ether, for example 10 to 30 mol %, a distillation pre-treatment is effective to provide methyl acetate having an a total acetaldehyde 1,1 dimethoxyethane impurity content of 0 to 100 ppm wt calculated as mass equivalents of acetaldehyde.

Methyl acetate having a total amount of acetaldehyde and 1,1 dimethoxyethane of 0 to 100 ppm wt calculated as mass equivalents of acetaldehyde may be fed directly as feed to a process for hydrolysing methyl acetate in the presence of at least one Brønsted acid catalyst to produce acetic acid without the need for further purification.

Methyl acetate having a total amount of acetaldehyde and 1,1 dimethoxyethane of 0 to 100 ppm wt calculated as mass equivalents of acetaldehyde may be fed directly as feed to a process for the conversion of methyl acetate and methanol by dehydration-hydrolysis in the presence of at least one Brønsted acid catalyst to co-produce acetic acid and dimethyl ether without the need for further purification.

A source of methanol is required for the dehydration-hydrolysis process. Methanol may be supplied as a combined feed with methyl acetate or as one or more separate feeds to the process. If methanol is supplied as a separate feed, it is preferred that it comprises mainly methanol but it may also comprise one or both of dimethyl ether and water.

The dehydration-hydrolysis process may be carried out utilising any desired molar ratio of methanol to methyl acetate but suitably the molar ratio of methanol:methyl acetate is in the range 1:0.1 to 1:20.

The dehydration-hydrolysis process may be carried out as a vapour phase process or as a liquid phase process, for example as a fixed bed process or a slurry phase process.

If it is desired to operate the dehydration-hydrolysis process as a vapour phase process, it is preferable to volatilise liquid feed(s), for example in a pre-heater prior to contact with the Brønsted acid catalyst.

The dehydration-hydrolysis process may be carried out at a temperature of from 100° C. to 350° C. Preferably, liquid phase processes are carried out at temperatures in the range 140° C. to 210° C. Preferably, vapour phase processes are conducted at temperatures in the range 150° C. to 350° C., for example in the range 200° C. to 280° C. or in the range 180 to 280° C.

The dehydration-hydrolysis process may be carried out at atmospheric pressure or at pressures greater than atmospheric. For liquid phase processes, it is preferred to operate the process at a total reaction pressure which is sufficient to maintain dimethyl ether product in solution. Suitable operating pressures are 40 to 100 barg (4000 to 10,000 kPa). For vapour phase processes, suitable operating pressures are in the range atmospheric to 30 barg (atmospheric to 3000 kPa).

Suitably, the dehydration-hydrolysis process is carried out at a gas hourly space velocity (GHSV) in the range 500 to 40,000 $h^{-1}$.

Suitably, the dehydration-hydrolysis process is carried out at a liquid hourly space velocity (LHSV) in the range 0.2 to 20 $h^{-1}$.

In one or more embodiments of the present invention, dehydration-hydrolysis is conducted as a vapour phase process at a temperature of from 150 to 350° C., for example of from 180 to 280° C. and at a pressure of atmospheric to 30 barg (atmospheric to 3000 kPa), for example 5 to 20 barg (500 kPa to 2000 kPa). Suitably, in such cases, the GHSV is in the range 500 to 40,000 $h^{-1}$.

In one or more embodiments of the present invention, dehydration-hydrolysis is conducted as a liquid phase process at a temperature of from 140 to 210° C. and at a pressure of 40 barg (4000 kPa) or higher, for example 40 to 100 barg (4000 kPa to 10,000 kPa). Suitably, in such cases, the LHSV is in the range 0.2 to 20 $h^{-1}$.

The dehydration-hydrolysis process may be carried out using any suitable technique and apparatus, for example by reactive distillation. Reactive distillation techniques and apparatus therefor are well-known. Typically, the feed, for example a feed comprising methyl acetate, methanol and optionally water, can be supplied to a conventional reactive distillation column operated, for example at a pressure in the range atmospheric to 20 barg (atmospheric to 2000 kPa) and at a reaction temperature in the range 100° C. to 350° C., to produce a crude reaction product comprising a mixture of acetic acid and dimethyl ether, which mixture is inherently separated within the reactive distillation column to recover a product stream rich in dimethyl ether, typically removed as an overhead from the column, and a product stream rich in acetic acid which is typically removed as a base stream from the column.

Alternatively, the dehydration-hydrolysis may be carried out in a fixed bed reactor or a slurry bed reactor.

The dehydration-hydrolysis process produces a crude reaction product comprising dimethyl ether and acetic acid. The crude reaction product may further comprise one or more of methyl acetate, methanol, water and acetaldehyde.

Depending on the pressure, dimethyl ether has a boiling point of −24° C. and acetic acid has a boiling point of 118° C. Owing to the difference in their boiling points, acetic acid and dimethyl ether may be recovered from the crude dehydration-hydrolysis reaction product by conventional purification methods, such as by distillation in one or more conventional distillation columns. Suitable distillation columns include tray or packed columns. The temperatures and pressures employed in the columns can vary. Suitably, a distillation column may be operated at a pressure, for example of atmospheric to 20 barg (0 to 2000 kPa). Typically, a stream rich in dimethyl ether is recovered as an overhead from the distillation column, and a stream rich in acetic acid is recovered as a base stream from the column.

One or both of the recovered dimethyl ether-rich and acetic acid-rich streams may comprise one or more of methanol, methyl acetate and water. These components may be removed from one or both of the dimethyl ether-rich and acetic acid-rich streams by conventional purification processes, such as by distillation in one or more distillation columns and re-utilised as recycle streams to processes utilised in the present invention such as one or both of carbonylation processes and dehydration-hydrolysis processes.

In one or more embodiments of the present invention, the crude reaction product of the dehydration-hydrolysis process is treated, suitably by a distillation method to recover an acetic-rich stream and a dimethyl ether-rich stream comprising dimethyl ether and acetaldehyde. In such cases, at least a part of the dimethyl ether-rich stream may be distilled, such as by fractional distillation, together with methyl acetate comprising acetaldehyde/1,1 dimethoxyethane impurities intended for use as a feed in the processes of the present invention to remove such impurities therefrom.

Acetic acid may be sold or may be used as a feedstock in a variety of chemical processes, such as the manufacture of vinyl acetate or ethyl acetate.

Dimethyl ether may be sold or used as a fuel or as a feedstock to carbonylation processes or to other chemical processes.

The hydrolysis and dehydration-hydrolysis processes may be operated as a continuous process or as a batch process, preferably operated as a continuous process.

The invention is now illustrated with reference to the following non-limiting Examples.

EXAMPLE 1

This Example demonstrates the effect of acetaldehyde impurities in feeds on the catalytic performance of zeolite catalysts utilised in the production of acetic acid.

The experiments were carried out in a reactor system capable of carrying out gas phase reactions on solid Brønsted acid catalysts. The system comprised 64 separate straight tube reactors of internal diameter of approximately 2 mm capable of holding between 0.01 and 0.1 g of solid catalyst material crushed and sieved to a size fraction between 100 and 200 microns.

The catalysts utilised in the reaction were alumina extrudates of the zeolites H-ZSM-5 and H-ferrierite. Prior to use, each of the catalysts were crushed and sieved to a particle size in the range 100-200 microns.

10 mg of a catalyst was placed in a reactor and heated for 1 hour under a flow of inert gas ($N_2$/He mixture) to a temperature of 180° C. at which point the gas feed to the reactor was replaced by a gaseous reaction feed comprising 20 mol % methanol and methyl acetate in a molar ratio of 1:1 and 80 mol % inert gas. Amounts of 1,1-dimethoxyethane ranging from 115 ppm wt to 2100 ppm wt were added to the reaction feed so as to provide total acetaldehyde and 1,1-dimethoxyethane concentrations as shown in Tables 1 and 2 below calculated as mass equivalents of acetaldehyde. The reaction was commenced with 56 ppm 1,1 dimethoxyethane in the feed under conditions of a temperature of 180° C. and a total pressure of 10 barg. After 96 hours the amount of 1,1-dimethoxyethane was increased to 703 ppm wt and the reaction continued for a further 96 hours at a temperature of 180° C. and at a total pressure of 10 barg.

The product stream from a reactor was periodically analysed by gas chromatography to provide composition data for feed and product components. The results of the experiments are shown in Tables 1 and 2 below. In the Tables 'STY' denotes space time yield to product dimethyl ether and acetic acid.

TABLE 1

| Catalyst | Time Period (Hours on Stream) | Mass equivalents of acetaldehyde (ppm wt) | Rate of dimethyl ether STY loss per day (g/kg/hr/day) | Rate of acetic acid STY loss per day (g/kg/hr/day) | Estimated catalyst lifetime to zero production (days) |
|---|---|---|---|---|---|
| H-ZSM-5 | 140-190 | 56 | 8 | 29 | 499 |
| H-ZSM-5 | 140-190 | 703 | 2072 | 360 | 2 |
| H-FER | 140-190 | 56 | 13 | 7 | 312 |
| H-FER | 140-190 | 703 | 61 | 31 | 65 |

TABLE 2

| Catalyst | Time Period (Hours on Stream) | Mass equivalents of acetaldehyde (ppm wt) | Rate of dimethyl ether STY loss per day (g/kg/hr/day) | Rate of acetic acid STY loss per day (g/kg/hr/day) | Estimated catalyst lifetime to zero production (days) |
|---|---|---|---|---|---|
| H-ZSM-5 | 140-225 | 56 | 12 | 28 | 291 |
| H-ZSM-5 | 225-250 | 1034 | 2751 | 478 | 1 |
| H-FER | 140-225 | 56 | 4 | 8 | 806 |
| H-FER | 225-300 | 1034 | 77 | 29 | 45 |

The results given in Tables 1 and 2 clearly demonstrate that the presence of more than a 100 ppm wt acetaldehyde is detrimental to the activity and lifetime of the zeolite catalysts.

EXAMPLE 2

A supported heteropolyacid catalyst was prepared by wet impregnation of a solution of 215 g silicotungstic acid (STA) in 488 g water onto a silica support (200 g) and allowed to stand for 1 hour before draining for 1 hour. The wet catalyst was then dried in an oven for 18 hours at 130° C. The dried catalyst was crushed and sieved to a particle range of 100-200 microns.

Using the apparatus as described in Example 1, 10 mg of the crushed and sieved catalyst was placed in a reactor and gradually heated to a temperature 180° C. over a period of approx. 250 hours under an inert gas stream ($N_2$/He mixture). The inert gas stream was replaced by a gaseous reaction feed stream comprising 20 mol % methanol and methyl acetate in a molar ratio of 1:1 and 80 mol % inert gas and at a total GHSV of 40,000 $h^{-1}$. The feed also contained 1,1-dimethoxyethane in amounts of 120 ppm wt and 260 ppm wt so as to provide total acetaldehyde and 1,1-dimethoxyethane concentrations as shown in Table 3 below calculated as mass equivalents of acetaldehyde.

The reaction was commenced with 59 ppm wt of 1,1 dimethoxyethane present in the feed and run for 45 hours at a temperature of 180° C. and at a total pressure of 10 barg. After 45 hours, the amount of 1,1-dimethoxyethane was increased to 127 ppm wt and the reaction continued under conditions of 180° C. and at a total pressure of 10 barg for a further 67 hours.

The product stream was periodically analysed by gas chromatography to provide composition data for feed and product components. The results of the experiments are shown in Table 3 below. In Table 3 'STY' denotes space time yield to product dimethyl ether and acetic acid.

TABLE 3

| Catalyst | Time Period (Hours on Stream) | Mass equivalents of acetaldehyde (ppm wt) | Rate of dimethyl ether STY loss per day (g/kg/hr/day) | Rate of acetic acid STY loss per day (g/kg/hr/day) |
|---|---|---|---|---|
| STA on Silica | 258-303 | 59 | 109 | 11 |
| | 303-370 | 127 | 261 | 26 |

EXAMPLE 3

The experiment in this Example 3 was carried out using a reactor system capable of carrying out gas phase reactions over solid Brønsted acid catalysts. The reactor system comprised a Hastelloy tube reactor of internal diameter of 15 mm with a central thermowell of 3 mm external diameter located through the entire length of the reactor and containing 7.17 g of ferrierite zeolite catalyst particles (length 10 mm and diameter 3.2 mm). The zeolite catalyst contained 3.1 wt % Cs. Voids between the catalyst particles were filled with small particles of inert silicon carbide The reactor was heated electrically and capable of temperatures up to 340° C. Pressure control of the reactor was achieved by means of a pressure control valve which could be used to regulate the pressure up to a total pressure of 40 barg.

The reaction was carried out by contacting the cesium ferrierite catalyst with a gaseous feed comprising approximately 70 mol % methyl acetate, 10 mol % methanol, 20 mol % water and 1,1 dimethoxyethane, The 1,1 dimethoxyethane was added in amounts of 146 ppm wt and 1010 ppm wt so as to provide total acetaldehyde and 1,1-dimethoxyethane concentrations as shown in Table 4 below.

The reaction conditions employed and maintained throughout the experiment were a temperature of 204° C., a reactant partial pressure of 9.0 bara with a gaseous distribution of 30-35% reactants and 60-65% inert gas ($N_2$/He mixture) and a reactant gas hourly space velocity (GHSV) of 1,500 $h^{-1}$.

The product stream was maintained in the vapour phase and periodically analysed for feed and product components using gas chromatography. The results are shown in Table 4 below. 'STY' denotes space time yield to product dimethyl ether and acetic acid.

TABLE 4

| Time Period (Hours on Stream) | Mass equivalents of acetaldehyde (ppm wt) | Rate of dimethyl ether STY loss per day (g/kg/hr/day) | Rate of acetic acid STY loss per day (g/kg/hr/day) | Estimated catalyst lifetime to zero production (days) |
|---|---|---|---|---|
| 0-192 | 494 | 1.9 | 3.7 | 134 |
| 192-767 | 71 | 0.2 | 0.2 | 1333 |

The results shown in Table 4 clearly demonstrate that the use of less than 100 ppm wt acetaldehyde provides significant improvement in the activity and lifetime of the zeolite catalyst.

EXAMPLE 4

This Example demonstrates a process for removing acetaldehyde impurities from a methyl acetate feed stream by treating the stream by distillation. A methyl acetate stream comprising mainly methyl acetate together with dimethyl ether and containing impurity levels of acetaldehyde, such as that which may be recovered from a process for the carbonylating dimethyl ether with a carbon monoxide-containing gas in the presence of a zeolite carbonylation catalyst, is fractionally distilled with methanol in a distillation column having 30 theoretical stages and equipped with a reboiler. The methyl acetate feed point to the distillation column is on stage 15 (counted from the head of the column). The column is operated at a pressure of 11.7 Barg, a heads temperature of 45° C. and a base temperature of 148° C. From the column is removed a heads stream comprising mainly dimethyl ether, a base stream comprising mainly methyl acetate with lesser amounts of water and acetaldehyde and a sidedraw stream which is removed on stage 6 of the column comprising the majority of the acetaldehyde originally present in the methyl acetate feed stream. A vent stream is taken from the column, condensed and a portion thereof is returned to the column at a reflux ratio of 2.1 and a boil-up ratio of 0.70. Utilising this procedure simulations were carried out using ASPEN software version 7.3. The flow rate of the various streams (in kmol/hr) is shown in Table 5 below. In Table 5 the following abbreviations are used:

MeOAc—methyl acetate
DME—dimethyl ether
AcOH—acetic acid
MeOH—methanol
AcH—acetaldehyde
$CO_x$—carbon oxides (carbon monoxide and carbon dioxide)
$H_2$—hydrogen As can be seen from the results provided in Table 5, use of the distillation method allows acetaldehyde to be concentrated up within the column with the majority removed as a component of the sidedraw stream. Methyl acetate so-treated can be directly utilised as a feed to processes which are catalysed by solid Brønsted acid catalysed and which utilise methyl acetate as a reactant therein such as processes for the hydrolysis of methyl acetate in the presence of solid Brønsted acid catalysts to produce acetic acid and processes for the co-production of acetic acid and dimethyl ether by the dehydration-hydrolysis of methyl acetate and methanol in the presence of solid Brønsted acid catalysts.

TABLE 5

| Stream (kmol/hr) | Feed stream | Vent stream | Heads stream | Base stream | Sidedraw stream |
|---|---|---|---|---|---|
| MeOAc | 8092 | 0.001 | 0.04 | 8080.6 | 11.4 |
| DME | 3917 | 322.3 | 3438.6 | 56.9 | 82.5 |
| Water | 2208 | 0 | 0.5 | 2204.2 | 3.2 |
| AcOH | 108 | 0 | 0 | 108 | 0 |
| MeOH | 927 | 0 | 0.2 | 926.2 | 0.6 |
| AcH | 5 | 0.035 | 1.3 | 1.6 | 2.1 |
| $CO_x$ | 199 | 72.4 | 126.5 | 0 | 0.3 |
| $H_2$ | 11 | 10.2 | 0.8 | 0 | 0 |

The invention claimed is:

1. A process for the dehydration-hydrolysis of methyl acetate and methanol to co-produce acetic acid and dimethyl ether which process is integrated with a carbonylation process for the production of methyl acetate which integrated process comprises the steps:
    a) carbonylating dimethyl ether with a carbon monoxide-containing gas in the presence of a zeolite carbonylation catalyst to produce a carbonylation reaction product and recovering methyl acetate therefrom;
    b) pre-treating at least a portion of the methyl acetate recovered in step (a) to reduce the amount of acetaldehyde and 1,1 dimethoxyethane impurities therein;
    c) converting methanol and methyl acetate by dehydration-hydrolysis in the presence of at least one Brønsted acid catalyst to co-produce acetic acid and dimethyl ether;
    in which dehydration-hydrolysis process the performance of the at least one Brønsted acid catalyst is improved by using as a methyl acetate feed methyl acetate pre-treated in step (b) in which the total amount of acetaldehyde and 1,1 dimethoxyethane impurities is maintained at 100 ppm wt or less calculated as mass equivalents of acetaldehyde,
    wherein each of the at least one Brønsted acid catalysts is a zeolite or a heteropolyacid.

2. A process according to claim 1 wherein the methyl acetate feed comprises 50 to 99 mol % methyl acetate, >0 to 45 mol % dimethyl ether and a total amount of acetaldehyde and 1,1 dimethoxyethane impurities of more than 100 ppm wt up to 1 wt % calculated as mass equivalents of acetaldehyde.

3. A process according to claim 1 wherein the methyl acetate feed is pre-treated to reduce the amount of impurities to less than 100 ppm wt calculated as mass equivalents of acetaldehyde.

4. A process according to claim 3 wherein the methyl acetate feed is pre-treated by a fractional distillation method.

5. A process according to claim 3 wherein methyl acetate comprising >0 to 80 mol % methyl acetate, a total amount of more than 100 ppm up to 1 wt % of acetaldehyde and 1,1 dimethoxyethane impurities and >0 to 50 mol % dimethyl ether is pre-treated to provide a methyl acetate feed having a total acetaldehyde and 1,1 dimethoxyethane impurity content of 0 to 100 ppm wt.

6. A process according to claim 5 wherein the methyl acetate to be pre-treated further comprises one or more of acetic acid, water, carbon oxides and hydrogen.

7. A process according to claim 1 wherein each Brønsted acid catalyst is a zeolite.

8. A process according to claim 7 wherein the zeolite of each Brønsted acid catalyst comprises at least one channel having a 10-membered ring.

9. A process according to claim 7 wherein the zeolite of each Brønsted acid catalyst has a framework type selected from FER and MFI.

10. A process according to claim 9 wherein the zeolite of each Brønsted acid catalyst has framework type FER and is selected from one or both of ferrierite and ZSM-35.

11. A process according to claim 7 wherein the zeolite of each Brønsted acid catalyst is in an exchanged form with one or more alkali metal cations.

12. A method according to claim 1 wherein each Brønsted acid catalyst is a heteropolyacid.

13. A process according to claim 1 wherein the methyl acetate feed further comprises one or both of methanol and water.

14. A process according to claim 13 wherein the methyl acetate feed further comprises one or more of carbon oxides, hydrogen and acetic acid.

15. A process according to claim 1 wherein the dehydration-hydrolysis process is carried out as a vapour phase process.

16. A process according to claim 1 wherein the process is carried out at a temperature of from 100 to 350° C.

17. A process according to claim 16 wherein the process is carried out at a temperature of 180 to 280° C.

18. A process according to claim 1 wherein the zeolite carbonylation catalyst comprises a zeolite which comprises at least one channel defined by an 8-membered ring.

* * * * *